United States Patent
Raskas

(10) Patent No.: US 8,965,470 B2
(45) Date of Patent: *Feb. 24, 2015

(54) MICRO-INVASIVE METHOD FOR PAINLESS DETECTION OF ANALYTES IN EXTRACELLULAR SPACE

(75) Inventor: Eric Jules Raskas, St. Louis, MO (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 874 days.

This patent is subject to a terminal disclaimer.

(21) Appl. No.: 12/219,228

(22) Filed: Jul. 17, 2008

(65) Prior Publication Data

US 2009/0093693 A1      Apr. 9, 2009

Related U.S. Application Data

(63) Continuation of application No. 11/104,666, filed on Apr. 13, 2005, now Pat. No. 7,409,238, which is a continuation of application No. 10/335,010, filed on Dec. 31, 2002, now Pat. No. 6,904,301, which is a (Continued)

(51) Int. Cl.
*A61B 5/1455*      (2006.01)
*G01N 21/85*       (2006.01)
(Continued)

(52) U.S. Cl.
CPC ........ *G01N 21/8507* (2013.01); *A61B 5/14514* (2013.01); *A61B 5/14532* (2013.01);
(Continued)

(58) Field of Classification Search
USPC ......... 600/309, 310, 316, 322, 344, 365, 473, 600/476
See application file for complete search history.

(56) References Cited

U.S. PATENT DOCUMENTS 4,014,321 A      3/1977 March
4,321,057 A      3/1982 Buckles
(Continued)

FOREIGN PATENT DOCUMENTS

CA      2 376 128      1/2009
DE      88 14 625      1/1989
(Continued)

OTHER PUBLICATIONS

S. Kayashima et al., "New transcutaneous sampling of glucose for patients with type II diabetes using an ion-sensitive field-effect transistor," *Clinica Chimica Acta*, vol. 240, 1995, pp. 11-19.
(Continued)

*Primary Examiner* — Eric Winakur
(74) *Attorney, Agent, or Firm* — Roylance, Abrams, Berdo & Goodman, L.L.P.

(57) ABSTRACT

A method of detecting at least one analyte in extra-cellular spaces includes the step of inserting a microprobe through the stratum corneum toward the stratum basale of the skin of a subject into extra-cellular spaces containing interstitial fluid having at least one analyte to be detected, said microprobe having a diameter at its tip no larger than approximately 10-50 microns. The method further includes optically testing for a predetermined analyte in the extra-cellular space adjacent the distal end of the microprobe without drawing a sample of the interstitial fluid. Preferably the microprobe body includes a sensor layer covering the distal optical tip of the microprobe body, the sensor layer being adapted to interact with a predetermined analyte to be detected in the interstitial fluid, and an optical detector responsive to interaction of the sensor layer with the predetermined analyte to signal detection of said predetermined analyte.

15 Claims, 3 Drawing Sheets

Related U.S. Application Data continuation of application No. 09/668,703, filed on Sep. 22, 2000, now Pat. No. 6,535,753, which is a continuation-in-part of application No. 09/143,258, filed on Aug. 20, 1998, now Pat. No. 6,197,257.

(51) Int. Cl.
*A61B 5/145* (2006.01)
*A61B 5/1459* (2006.01)
*A61B 5/00* (2006.01)
*A61B 10/00* (2006.01)

(52) U.S. Cl.
CPC .......... *A61B5/14546* (2013.01); *A61B 5/1455* (2013.01); *A61B 5/1459* (2013.01); *A61B 5/6825* (2013.01); *A61B 10/0045* (2013.01); *A61B 2010/008* (2013.01); *A61B 2562/12* (2013.01)
USPC ........................................................ 600/310

(56) References Cited

U.S. PATENT DOCUMENTS

| | | |
|---|---|---|
| 4,460,684 A * | 7/1984 | Bauer .............................. 435/14 |
| 4,637,403 A | 1/1987 | Garcia et al. |
| 4,655,225 A | 4/1987 | Dahne et al. |
| 4,671,288 A | 6/1987 | Gough |
| 4,752,115 A | 6/1988 | Murray et al. |
| 4,805,623 A | 2/1989 | Jobsis |
| 4,882,492 A | 11/1989 | Schlager |
| 4,886,338 A | 12/1989 | Yafuso et al. |
| 4,925,268 A | 5/1990 | Iyer et al. |
| 4,981,779 A | 1/1991 | Wagner |
| 4,999,306 A | 3/1991 | Yafuso et al. |
| 5,000,901 A | 3/1991 | Iyer et al. |
| 5,001,054 A | 3/1991 | Wagner |
| 5,029,583 A | 7/1991 | Meserol et al. |
| 5,127,077 A | 6/1992 | Iyer et al. |
| 5,143,066 A | 9/1992 | Komives et al. |
| 5,179,951 A | 1/1993 | Knudson |
| 5,271,073 A | 12/1993 | Hui et al. |
| 5,341,805 A | 8/1994 | Stavridi et al. |
| 5,342,789 A | 8/1994 | Chick et al. |
| 5,361,314 A | 11/1994 | Kopelman et al. |
| 5,398,681 A | 3/1995 | Kupershmidt |
| 5,434,084 A | 7/1995 | Burgess, Jr. |
| 5,448,992 A | 9/1995 | Kupershmidt |
| 5,517,313 A | 5/1996 | Colvin, Jr. |
| 5,529,755 A | 6/1996 | Higashio et al. |
| 5,533,509 A | 7/1996 | Koashi et al. |
| 5,553,613 A | 9/1996 | Parker |
| 5,553,616 A | 9/1996 | Ham et al. |
| 5,582,184 A | 12/1996 | Erickson et al. |
| 5,605,152 A | 2/1997 | Slate et al. |
| 5,617,852 A | 4/1997 | MacGregor |
| 5,627,922 A | 5/1997 | Kopelman et al. |
| 5,680,858 A | 10/1997 | Hansen et al. |
| 5,695,949 A | 12/1997 | Galen et al. |
| 5,718,842 A | 2/1998 | Papkovsky et al. |
| 5,746,217 A | 5/1998 | Erickson et al. |
| 5,817,089 A | 10/1998 | Tankovich et al. |
| 5,820,570 A | 10/1998 | Erickson et al. |
| 5,846,486 A | 12/1998 | Pugh |
| 5,859,937 A | 1/1999 | Nomura |
| 5,879,367 A | 3/1999 | Latterell et al. |
| 5,894,351 A | 4/1999 | Colvin, Jr. |
| 5,910,661 A | 6/1999 | Colvin, Jr. |
| 5,954,643 A | 9/1999 | VanAntwerp et al. |
| 5,982,959 A | 11/1999 | Hopenfeld |
| 6,014,577 A | 1/2000 | Henning et al. |
| 6,040,194 A | 3/2000 | Chick et al. |
| 6,091,975 A | 7/2000 | Daddona et al. |
| 6,103,535 A | 8/2000 | Pilevar et al. |
| 6,119,031 A | 9/2000 | Crowley |
| 6,157,442 A | 12/2000 | Raskas |
| 6,197,257 B1 | 3/2001 | Raskas |
| 6,197,534 B1 | 3/2001 | Lakowicz et al. |
| 6,248,067 B1 | 6/2001 | Causey et al. |
| 6,277,627 B1 | 8/2001 | Hellinga |
| 6,334,856 B1 | 1/2002 | Allen et al. |
| 6,382,555 B1 | 5/2002 | Domen |
| 6,383,767 B1 | 5/2002 | Polak |
| 6,521,446 B2 | 2/2003 | Hellinga |
| 6,535,753 B1 | 3/2003 | Raskas |
| 6,584,335 B1 | 6/2003 | Haar et al. |
| 6,904,301 B2 | 6/2005 | Raskas |
| 6,922,576 B2 | 7/2005 | Raskas |

FOREIGN PATENT DOCUMENTS

| | | |
|---|---|---|
| DE | 195 38 145 | 3/1996 |
| EP | 0 073 558 | 3/1983 |
| EP | 0 409 033 | 1/1991 |
| EP | 0 709 659 | 5/1996 |
| EP | 0 864 363 | 9/1998 |
| JP | 03-089150 | 4/1991 |
| JP | 09-145617 | 6/1997 |
| JP | 4163853 | 10/2008 |
| WO | WO 98/22805 | 5/1998 |
| WO | WO 99/07277 | 2/1999 |
| WO | WO 99/64580 | 12/1999 |
| WO | WO 00/11453 | 3/2000 |
| WO | WO 03/035891 | 5/2003 |
| WO | WO 03/057734 | 7/2003 |
| WO | WO 03/057850 | 7/2003 |
| WO | WO 03/057851 | 7/2003 |

OTHER PUBLICATIONS

A. Laurent et al., "Echographic measurement of skin thickness in adults by high frequency ultrasound to assess the appropriate microneedle length for intradermal delivery of vaccines," *Vaccine*, vol. 25, 2007, pp. 6423-6430.

Zeev Rosenzweig and Raoul Kopelman, "Analytical Properties and Sensor Effects of a Micrometer-Sized Optical Fiber Glucose Biosensor," *Analytical Chemistry*, vol. No. 8, Apr. 1996, pp. 1408-1413.

F. John Service, Peter C. O'Brien, Steven D. Wise, Sheryl Ness, Suzanne M. LeBlanc, "Dermal Interstitial Glucose as an Indicator of Ambient Glycemia," *Diabetes Care*, vol. 20, No. 9, Sep. 1997, pp. 1426-1429.

* cited by examiner

MICRO-INVASIVE METHOD FOR PAINLESS DETECTION OF ANALYTES IN EXTRACELLULAR SPACE

CROSS-REFERENCE TO RELATED APPLICATION

This application is a continuation of U.S. patent application Ser. No. 11/104,666, filed Apr. 13, 2005, now U.S. Pat. No. 7,409,238 which is a continuation of U.S. patent application Ser. No. 10/355,010, filed Dec. 31, 2002 (now U.S. Pat. No. 6,904,301), which is a continuation of U.S. patent application Ser. No. 09/688,703, filed Sept. 22, 2000 (now U.S. Pat. No. 6,535,753), which is a continuation-in-part of U.S. Pat. application Ser. No. 09/143,258,filed Aug. 20, 1998 (now U.S. Pat. No. 6,197,257) on Micro Sensor Device.

STATEMENT REGARDING FEDERALLY SPONSORED RESEARCH OR DEVELOPMENT

Not Applicable.

BACKGROUND OF THE INVENTION

1. Field of the Invention

This invention relates generally to a method and apparatus for detection of analytes, and more particularly to such method and apparatus for the painless detection of such analytes in extracellular space.

2. Description of the Prior Art

The past decade has seen an increased effort for new and less invasive means of detecting relevant compounds in biological systems. In the past such detection has involved clinical assays using in vitro diagnostics requiring invasive sampling methods. Newer philosophies in medicine and related disciplines have tended to use less invasive means that are more comfortable to the subject and which tend to reduce the possibility of transmission of infection.

It is known in the art to use non-invasive spectral techniques to quantitatively determine the presence and concentration of analytes. For example, U.S. Pat. No. 4,882,492 to Schlager teaches a non-invasive near-infrared measurement of blood analyte concentrations, in particular the measurement of blood glucose levels. Schiager recognizes that certain wavelengths of light in the near-infrared spectrum are absorbed by glucose. In that patent, modulated light is directed against a tissue (such as an earlobe). Some portion of the light is passed through the tissue and its spectrum is modified in response to the amount of glucose in the blood and tissue. Similar approaches are shown in U.S. Pat. No. 4,014,321 to March, U.S. Pat. No. 4,655,225 to Dahne et al., U.S. Pat. No. 4,805,623 to Jobsis, and U.S. Pat. No. 5,179,951 to Knudson. However methods using various parts of the infrared spectrum for detecting some analytes are relatively unproven to date due to their inability to differentiate multiple occurrences of the analytes at different concentration levels in different body compartments using the available spectral data.

Cygnus, Inc. has demonstrated a technique for collection of glucose in interstitial fluid found in extra cellular space. This technique uses reverse ionopherisis to attract heavier salt molecules to the outside surface of the skin and uses electrochemical means for detecting glucose. This method is currently the subject of an FDA PMA review. One drawback of this method is the initial time delay for retrieval of sufficient fluid for sampling. This method also requires the subject to constantly have a device in place for collection of the fluid.

SpectRx has developed an alternative method for accessing the interstitial fluid by using a laser to ablate small apertures in the surface of the skin sufficient to release interstitial fluid from extra cellular space. Although this method has also produced data which correlates well with constituents found in blood, it suffers from a progressive closure of the aperture and a correlation between sufficient aperture size and the amount of discomfort caused by the initial ablation of the skin.

TCPI has developed a method similar to that of Cygnus which draws interstitial fluid outside the skin. This method however uses a replaceable patch that changes colormetrically according to the presence of the analyte. This method also requires several minutes more than present blood testing methods.

Integ has disclosed a method to access interstitial fluid in an intradermal layer, sampling the interstitial fluid by drawing interstitial fluid through a capillary and then testing the fluid in situ or extracting the fluid to an external apparatus. The Integ method may be prone to rupture of small capillaries that are found in the upper layers of the dermis and to contact with nerve endings that abut the dermal/epidermal junction. There has also been controversial data produced as to whether glucose levels in particular track well between levels produced in the intradermal interstitial fluid and that found in capillaries or veins. Apparently the Integ method draws a one microliter sample from the interstitial fluid, which sample is analyzed for glucose.

In summary, the prior art methods could be improved in that they suffer from insufficient sampling quantities, delayed periods of testing required for sample collection, destruction of skin cells at the stratum corneum level, discomfort to the subject, and the production of quantities of blood.

SUMMARY OF THE INVENTION

Among the various objects and features of the present invention may be noted the provision of a method and apparatus for detecting analytes in extra cellular space which overcomes the problems associated with sampling.

Another object is the provision of such a method and apparatus which substantially reduces or eliminates delay time before detection can be accomplished which in the prior art results from the necessary delay for sample collection.

A third object is the provision of such a method and apparatus which prevents the destruction of skin cells at the stratum corneum level.

A fourth object is the provision of such a method and apparatus which reduces or eliminates discomfort of the subject.

A fifth object is the provision of such a method and apparatus which reduces or eliminates the production of quantities of blood during the testing.

Other objects and features will be in part apparent and in part pointed out hereinafter.

Briefly, the new method is a micro invasive detection of analytes in extra-cellular spaces that are on the epidermal side of the epidermal/dermal junction. Although the initial (outermost) layer of the epidermis at the surface of mammalian skin is considered to be a non-nucleated (dead) strata of cells known as the stratum corneum, there are several layers of the epidermis with those closer to the stratum basale, the layer that precedes the epidermal/dermal junction, all found to be living cells requiring nutrients from extra-cellular space.

BRIEF DESCRIPTION OF THE DRAWINGS

Similar reference characters indicate similar parts throughout the several views of the drawings.

DESCRIPTION OF THE PREFERRED EMBODIMENT

Figure 1:
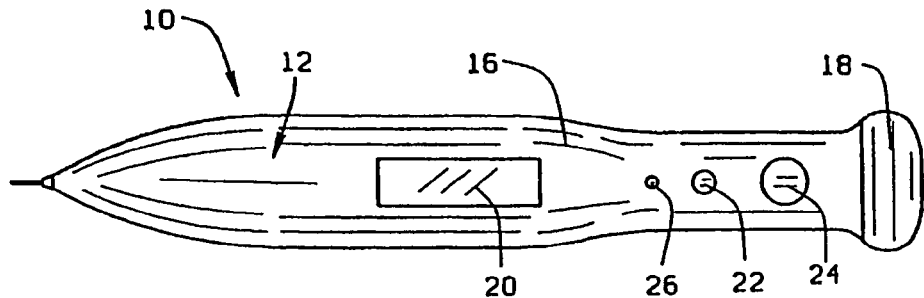
FIG. 1 is a perspective view of a micro sensor device constructed according to the present invention.

Referring now to the drawings, wherein like numbers refer to like items, number 10 identifies a preferred embodiment of a micro sensor device constructed according to the present invention. As illustrated in FIG. 1, the device 10 comprises a pencil or pen shaped body 12 which includes an integrated sensor head 14, a central body portion 16, and an end cap 18. The central body portion 16 further includes a display device 20, such as an LED (light emitting diode) type display or an LCD (liquid crystal display) type display, for displaying information. The end cap 18, which may be removable from the central body portion 16, is used to allow access into the interior of the central body portion 16. Batteries (not shown) can be inserted into the central body portion 16 to supply power to the device 10, as will be explained. The central body portion 16 may also include an ON/OFF switch 22 which may be used to operate the device 10, a speaker 24 which may be to audibly indicate certain information, and an LED 26 which may be used to indicate that a reading has been completed. Other switches (not shown) may be incorporated into the central body portion 16 to further control the device 10. Additionally, the central body portion 16 houses electronic circuitry and other components which will be illustrated and explained in further detail herein. The device 10 is sized and shaped to be a hand held type device that is portable and preferably is the size and shape of a pencil or a pen.

Figure 2:
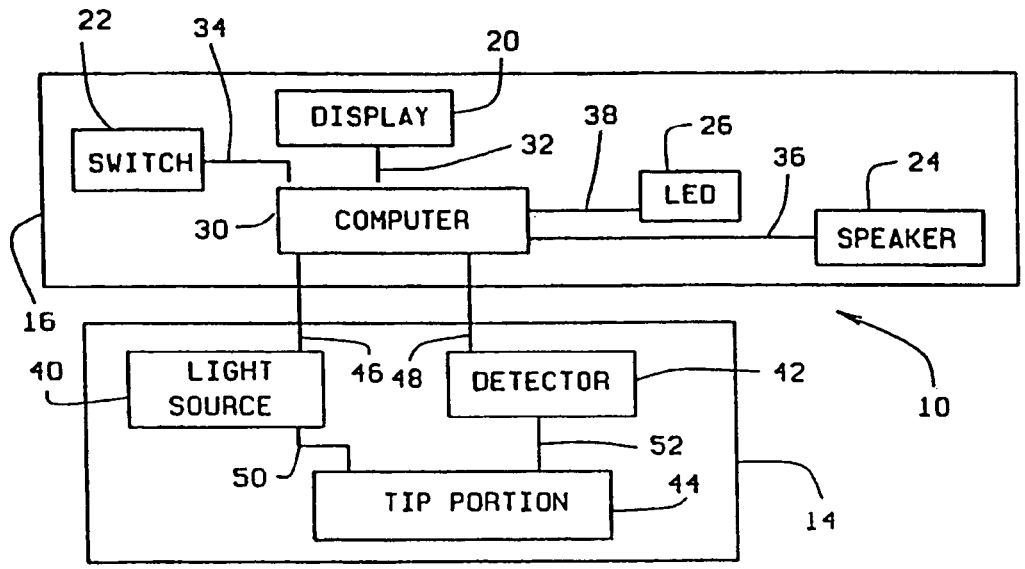
FIG. 2 is a block diagram of the micro sensor device constructed according to the present invention.

With reference now to FIG. 2, a block diagram of the circuitry and components of the device 10 is shown. The device 10 includes a computer 30 which is connected to the display 20 by a wire 32, to the switch 22 by a wire 34, to the speaker 24 by a wire 36, and to the LED 26 by a wire 38. The computer 30 may consists of, by way of examples, a microprocessor, a microcontroller, an ASIC chip, or any other known equivalent device which is capable of processing electrical signals. The computer 30 may also be connected to a power supply, such as a battery, although the power supply and such connection are not illustrated in FIG. 2.

Additionally, the computer 30 may also be connected to other switches (not shown) which may be provided with the device 10 to further control or operate the device 10. The computer 30 and the other components 20, 22, 24, and 26 are all housed within the central body portion 16.

The integrated sensor head 14 comprises a light source, a detector 42, and a tip portion 44 all incorporated or integrated within the integrated sensor head 14. For example, the integrated sensor head 14 may be formed by any suitable injection molding method or technique. Additionally, the integrated sensor head 14 is of an extremely small size on the order of about under 30 microns in size. The light source 40 is operatively connected to the computer 30 by an electrical connection 46 and the detector 42 is likewise electrically connected to the computer 30 by an electrical connection 48. The tip portion 44 consists of an extremely small needle shaped analyte. The light source 40 may be an LED, a laser, a laser diode, or other light excitation source. The light source 40 is adapted to project a beam of light 50 into the tip portion 44. The beam of light 50 passes through the tip portion 44 and a reflected pattern of light 52 may be reflected back from a sample (not shown) through the tip portion 44 to the detector 42. The detector 42 provides the reflected pattern of light 52 to the computer 30 for processing to determine the concentration of material within a sample. The detector 42 may be, for example, a photodiode, a miniature spectrometer, or any other device which may detect light.

Figure 3:
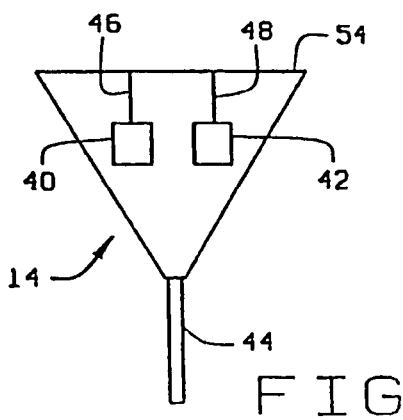
FIG. 3 is a perspective view of a tip portion of the micro sensor device shown in FIG. 1.

The integrated sensor head 14 is shown in greater detail in FIG. 3 and again is preferably a small device on the order of under 30 microns in size or diameter. In particular, the sensor head 14 is of unitary construction having the light source 40, detector 42, and tip portion 44 incorporated therein. The electrical connections 46 and 48 extend from the light source 40 and the detector 42, respectively, and terminate at a first end 54 of the sensor head 14. In this manner, the connections 46 and 48 mate with corresponding connections or terminals (not shown) in the central body portion 16. The use of the electrical connections 46 and 48 eliminates any alignment problems which would been associated with other types of connectors, such as an optical connection. Additionally, the sensor head 14 is mated or connected to the central body portion 16 in any suitable manner, as for example by screw type attachment or even frictional engagement.

The tip portion 44 may be chemically treated or use an enzymatic process or treatment which enables the tip portion 44 to interact with the sample to be detected or monitored. Properties of the tip portion 44 may vary dependent upon the sample and the chemical or substance to be detected by the device 10. As constructed and with particular reference to FIG. 2, the tip portion 44 allows for the beam of light 50 to pass through and the reflected pattern of light 52 to be reflected through the tip portion 44. As indicated above, the tip portion 44 is extremely small and because of its size it can be inserted through gaps in between most cells or through the membrane of a cell without, damaging the cell. Additionally, the tip portion is small enough that when it is inserted into a human, for example a human hand, there will be little or no sensation felt.

The tip portion 44 may have specific chemical sensitivities based upon the properties of a dye matrix. A dye may be chemically activated by a different chemical compound which enables sensing of a specific chemical property within a sample or a substance. The tip portion 44 provides for enhanced sensitivity, selectivity, and stability when detecting a concentration within a sample or substance. In this manner, the sensor device 10 interacts with the substance or sample to detect a specific chemical or concentration within the substance. Some examples of how the tip portion 44 may be chemically treated to have specific chemical sensitivities or to interact with the sample to be detected or monitored may be found in U.S. Pat. Nos. 5,361,314 and 5,627,922.

Figure 4:
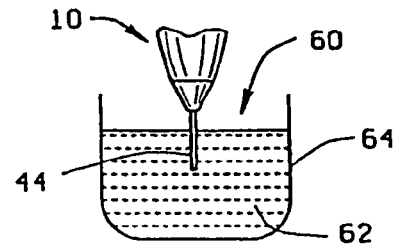
FIG. 4 is a schematic view of the micro sensor device of the present invention being employed to sense a concentration in a sample.

With reference now to FIGS. 1, 2, and 4, the operation of the device 10 will be explained in detail. In order to operate the device 10, the on/off switch 22 is pressed to initialize the device 10. Once powered, the device 10 may be inserted into a sample 60 to test for a particular concentration of material within the sample 60. As shown in FIG. 4, the sample to be tested is a liquid 62 in a beaker 64. The tip portion 44 is inserted into the liquid 62 and at this point in time a beam of light, such as the beam of light 50, is transmitted into the liquid 62. With the tip portion 44 being in contact with the liquid 62, the liquid 62 reacts chemically with the tip portion 44 and the color of the chemical composing the sensor device 10 changes. As a result of this change, the pattern of the light reflected back into the tip portion 44 changes, such as that shown by the pattern of reflected light 52. This pattern is sensed by the detector 42 and signals are provided to the computer 30 which performs a calculation to determine the concentration of the particular chemical being sensed and the result may be displayed in the display 20.

Additionally, the chemical properties of the tip portion 44 of the sensor portion 14 may be changed to react with another chemical to detect some other chemical within a sample. Further, instead of changing the chemical properties of the tip portion 44, it may only be necessary to change the light source 40 to detect some other chemical within a sample. It is also possible to have a cap (not shown) which covers the tip portion 44 when the device 10 is not in use. The cap may also have incorporated therein a mechanism for keeping the tip portion 44 sterilized.

The tip portion 44 may be constructed by using any suitable injection molding method or technique and precision injection molding methods for molding extremely small parts may be employed. Another method or technique for constructing the tip portion 44 may include a micro fabrication process known as micro-electro-mechanical systems (MEMS) fabrication process wherein an extremely small sized part may be carved out of a substance. Even a micro-electro-mechanical system (MOEMS) may be used to produce the tip portion 44. Additionally, the tip portion 44 may be manufactured from silicas, plastics, polymers, or even pyrex. Other known methods for construction of the tip portion may be a heat drawn process or even swaging.

Figure 5:
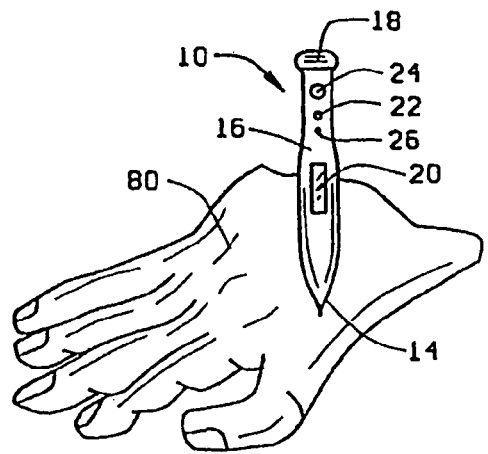
FIG. 5 is perspective view of the micro sensor device of FIG. 1 illustrated monitoring a concentration of glucose in a hand of a patient.

Referring now to FIG. 5, the sensor device 10 is again shown having a pencil like body 12 which includes the central body portion 16, the end cap 18, and the sensor head 14 which has been inserted into a hand 80 in order to detect the presence of a concentration of material, such as for example glucose. The central body portion 16 includes the display 20 for displaying information such as glucose concentration, the ON/OFF switch 22 for operating the device 10, the speaker 24, and the LED 26. The tip portion 14 is shown being inserted into the hand 80 and because of its extremely small size little or no sensation will be felt. The other components of the sensor device 10, which were discussed with reference to FIG. 2, are all housed within the central body portion 16 and the tip portion 14.

Once inserted into the hand 80, actuation of the sensor device 10 will cause the computer 30 to operate the light source 40. The light beam 50 is produced and sent through the tip portion 44. With the tip portion 44 being in contact with the hand 80, the tip portion 44 reacts chemically and the pattern of light 52 is generated and reflected back through the tip portion 44 to the detector 42. The detector 42 transmits the pattern of light 52 to the computer 30 which then calculates the concentration of glucose within the hand 80. The result may be displayed in the display 20 or audibly indicated by the speaker 24. Once the result is indicated the device 10 may be removed from the hand 80 and turned off.

Figure 6:
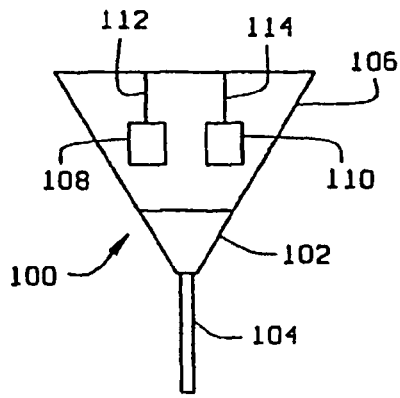
FIG. 6 is a block diagram of another embodiment of the integrated sensor head constructed according to the present invention.

FIG. 6 illustrates another embodiment of an integrated sensor head 100 which may be used with the device 10. The sensor head 100 comprises a first integrated portion 102 which includes a tip portion 104 and a second integrated portion 106 which includes a light source 108, a detector 110, and connectors 112 and 114 which are connected to the light source 108 and the detector 110, respectively. The first integrated portion 102 may be connected to the second integrated portion 106 by any suitable method or constructions, such as by a screw type construction. In this embodiment the first integrated portion 102 is easily removable from the second integrated portion 106 and the first integrated portion 102 may be interchanged with new first integrated portions 102 as need be. For example, the tip portion 104 of the first integrated portion 102 may lose its effectiveness over time, degrade, or become contaminated and removal of the first integrated portion 102 is all that will be required to change to a new tip portion 104. In this manner, the sensor head 100 has the feature of a replaceable tip portion 104. Additionally, the first integrated portion 102 including the tip portion 104 is disposable and easily discarded from second integrated portion 106. The second tip portion 106 incorporates the light source 108, the detector 110, and the connectors 112 and 114 and there is no need to replace these elements 106-114 in this embodiment.

Figure 7:
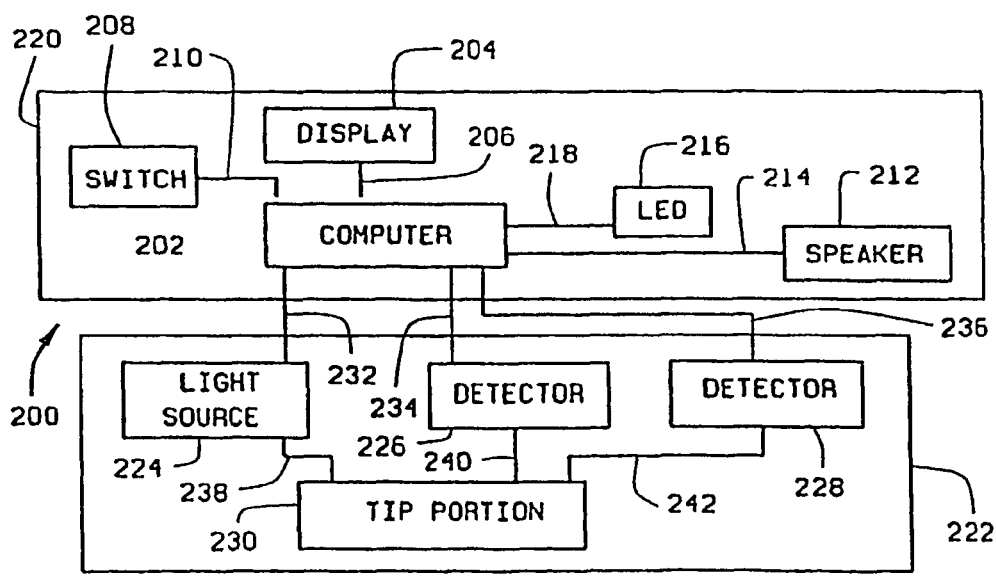
FIG. 7 is a block diagram of a second embodiment of the micro sensor device constructed according to the present invention.

FIG. 7 depicts a block diagram of another embodiment of a micro sensor device 200. The sensor device 200 comprises a computer 202 which is connected to a display device 204 by a wire 206, to a power switch 208 by a wire 210, to a speaker 212 by a wire 214, and to an LED 216 by a wire 218. The computer 202 may consists of, by way of examples, a microprocessor, a microcontroller, an ASIC chip, or any other known equivalent device which is capable of processing electrical signals and controlling various output devices or components. The computer 202 may also be connected to a power supply, such as a battery or a rechargeable battery, although the power supply and such connection are not illustrated in FIG. 7. Additionally, the computer 202 may also be connected to other switches (not shown) which may be provided with the device 200 to further control or operate the device 200. The computer 202 and the other components 204, 208, 212, and 216 are all housed within a central body portion 220 of the device 200.

An integrated sensor head 222 is connected to the central body portion 220 by any suitable means. The integrated sensor head 222 comprises a light source 224, a first detector 226, a second detector 228, and a tip portion 230 all incorporated or integrated within the integrated sensor head 222. For example, the integrated sensor head 14 may be formed by any suitable injection molding method or technique. Additionally, the integrated sensor head 222 is of an extremely small size on the order of about under 30 microns in size. The light source 224 is operatively connected to the computer 202 by an electrical connection 232 and the first detector 226 is likewise electrically connected to the computer 202 by an electrical connection 234. The second detector 228 is also connected or interfaced to the computer 202 by a connection 236. The tip portion 230 consists of an extremely small needle shaped analyte. The light source 224 may be an LED, a laser, a laser diode, or other light excitation source. The light source 224 is adapted to project a beam of light 238 into the tip portion 230. The beam of light 228 passes through the tip portion 230 and a first reflected pattern of light 240 may be reflected back from a sample (not shown) through the tip portion 230 to the first detector 226. The first detector 226 provides the first reflected pattern of light 240 to the computer 202 via the connection 234 for processing to determine the concentration of material within a sample.

Additionally, a second reflected pattern of light 242 may be produced and reflected back from a sample (not shown) through the tip portion 230 to the second detector 228. The second detector 228 provides the second reflected pattern of light 242 to the computer 202 via the connection 236 for processing to determine the concentration of material within a sample.

Examples of the first detector 226 and the second detector 228 were previously noted above with respect to the detector 42. In this manner, two different substances may be monitored or detected by the device 200. Although the device 200 is depicted to show the monitoring of at least two different chemical compounds or substances it is also contemplated that more than two chemical compounds or substances may be sensed, detected, or monitored by the device 200 by adding additional components, as has been taught and illustrated.

Although not illustrated, it is also possible and contemplated to have an integrated head sensor which has the light source 224 and the two detectors 226 and 228 incorporated within a first integrated head portion and the tip portion 230 incorporated within a second integrated head portion which is separable from the first integrated head portion. In this manner, the second integrated head portion in essence becomes a disposable component of the micro sensor device.

Figure 8:
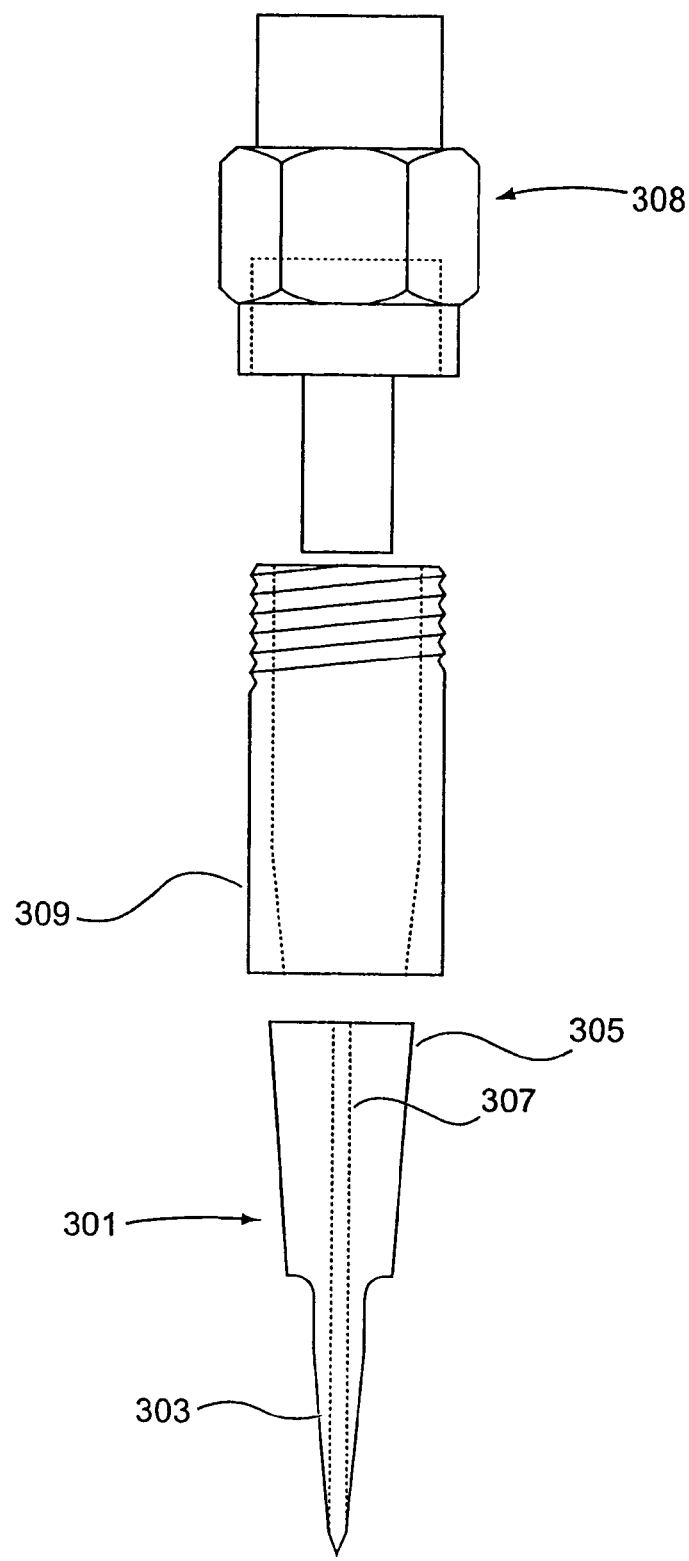
FIG. 8 is an exploded view of an optical member for use in the present invention suitably designed for connection to a standard SMA connector.

It is preferred that the method of the present invention uses an optical member, such as the previously shown optical members or more preferably such as microprobe 301 shown in FIG. 8, that has been fabricated to have a tip size less than 20 microns to enter at the stratum corneum and rest in or proximal of extracellular space of the stratum basale of the epidermis. Microprobe 301 includes a distal tip portion 303 extending proximally 9.8914 mm to a base portion 305. Both base portion 305 and tip portion 303 are tapered, with a substantial step where the tip portion meets the base portion. Base portion 305 has a width of 5.1068 mm at its proximal end and a length of 9.5791 mm, and tapers at approximately four degrees to the step where it meets the tip portion 303.

It is preferred that the optical member be molded to the final shape, preferably using a two-part RTV rubber silicone mold using known molding techniques. That mold is prepared using a hard durometer type silicone such as that sold under the trade designation G-380 by Silicones, Inc. Such a silicone is suitable for small parts. The first part of the mold is prepared by creating a pattern from a modified micropipette tip and a pulled silica optical fiber tip 307. Specifically the micropipette tip is an Eppendorf-style tip that has been trimmed at the bottom to expand the diameter to approximately 600 microns. The pulled silica optical fiber tip 307 is made from silica fiber having a diameter of 600 microns (such fibers are available from 3M). The fiber is placed into an optical fiber puller such as that sold under the trade designation P2000 by Sutter Instruments. The tip is pulled so that the fiber tapers from 600 microns down to 10-50 microns at its extreme tip. The silica pulled tip is then placed into the Eppendorf-style pipette tip and held in place by friction. This pattern (pipette tip plus pulled fiber tip) is then placed into a glass vial that has been filled with the RTV silicone to form the first part of the mold.

The second part of the mold is prepared by taking a standard optical fiber SMA connector 308 and removing the lock nut from the assembly. The remaining portion of the assembly (minus the lock nut) is placed as a cover on the poured mold containing the optical member pattern. After curing and removal of the SMA connector, the mold is then refilled in the female impression that has remained from the SMA connector. The final part is a male SMA silicone molded piece 309 (FIG. 8) that custom fits the first part of the mold.

Alternatively, the mold can be made using machining or stereolithography or other conventional techniques.

The optical pattern is then removed from the first part of the mold and replaced by another silica optical fiber piece 307 that has been tapered in an identical manner and has been measured to be the length from the tip of the mold to abut against the face of the second part of the mold. This tapered fiber is then placed inside the mold and remains there as a permanent portion of the final part. The body of the final part is then poured using a hard durometer polyurethane such as that sold under the trade designation IE-71DC by Innovative Polymers. The second part of the mold is then placed into the first part of the mold, during the cure process. After curing, the final part is manually released from the mold and is ready for application of the sensor chemistry.

Unlike methods used to penetrate through the epidermal/dermal junction, which can access capillary structures, the present method has no possibility of accessing capillaries since the capillaries do not extend beyond the epidermal/dermal junction. In addition the present method has no possibility of exciting nerve endings since the nerve endings are all found beneath the epidermal/dermal junction. The molded part is covered with a sensor layer that is designed to target a specific analyte(s) in the extra-cellular space of the epidermis. By way of illustration, the following analytes are among the many which may be targeted:

ACETALDEHYDE
Acetate
Acetic Acid
ADENOSINE 5'-MONOPHOSPHATE
ALANINE
ALCOHOL ESTER
ALIPHATIC NITRO COMPOUNDS
ALKALINE PHOSPHATASE
ALLYL ALCOHOL
ALTRONOLACTONE
AMINO ACIDS
Aminophenol
AMMONIA
AMP
AMYLAMINE
AMYLASE
ARGININE
Aromatic Amine
Aromatic Diamine
ARSENATE
ASCORBIC ACID
ASPARTATE
BENZALDEHYDE
Benzidine
BENZYLAMINE
BORATE
BUTANOL
BUTYLAMINE
CADAVERIN
Carbohydrate
Catechol
Chlorogenic Acid
CHOLESTEROL
CHOLINE
CHOLINESTERASE
CHYMOTRYPSIN
Cresol
DEXTRAN
Dextrose
DIAMINE
Dianisidine
DIHYDRO-OROTATE
DIHYDROXYACETONE -continued Dihydroxyphenylalanine
DIOXY-D-GLUCOSE
DIOXY-FLUORO-D-GLUCOSE
Dopamine
EMULSIN
ERYTHROSE
ETHANOL
ETHYL MERCAPTAN
FORMALDEHYDE
FORMIC ACID
FRUCTOSE
FURFURAL
FURFURYL ALCOHOL
GALACTONOLACTONE
GALACTOSE
GLUTAMIC ACID
GLUCONO-LACTONE
GLUCOPYRANOSE
GLUCORONIDASE
GLUCOSE
GLUCOSE-6-PHOSPHATE
GLUCOSIDASE
GLUTAMATE
GLUTAMATE PYRUVATE TRANSAMINASE
GLYCERALDEHYDE
GLYCERIN
GLYCEROL
GLYCOLATE
GLYOXYLATE
HEXYLAMINE
HISTAMINE
HISTIDINE
HYDROGEN PEROXIDE
Hydroquinone
HYDROXYMETHYL FURFURAL
HYDROXYPHENYLACETIC ACID
HYDROXYPHENYLLACTIC ACID
HYPOXANTHINE
HYDROXY ACIDS
INORGANIC PHOSPHORUS
ISOBUTYLAMINE
ISOPROPANOL
LACTASE
Lactate
LACTATE DEHYDROGENASE
Lactic Acid
LACTOSE
LEUCINE
LIPASE
LYSINE
LYSINE DECARBOXYLASE
MALTOSE
MANDALATE
MANNOSE
MANNONOLACTONE
MELIBIOSE
METHANOL
METHIONINE
METHYL SULFATE
METHYL-D-GLUCOSE
METHYL-L-AMINO ACIDS
METHYLCATECHOL
MOLYBDATE
MONOAMINE
MONOMETHYL SULFATE
N,N-diethyl-p-phenylenediamine
N,N-dimethyl-p-phenylenediamine
NAD
NADH
NADPH
NITROETHANE
OCTYLAMINE
OXALATE
OXALIC ACID
PECTIN
PECTIN ESTERASE
Phenol
Phenylalanine
Phenylenediamine -continued PHOSPHATE
PHOSPHATIDYL CHOLINE
POLYAMINE
PROLINE
PROPANOL
PROPYLAMINE
PURINE
PUTRESCIN
PYRIDOXAMINE PHOSPHATE
Pyrocatechol
Pyrogallol
PYRUVATE
PYRUVIC ACID
RAFFINOSE
SALICIN
SARCOSINE
SORBOSE
SPERMIDINE
SPERMINE
STARCH
SUCROSE
SULFITE
THIAMINE
TREHALOSE
TRYPTOPHAN
TUNGSTATE
TYRAMINE
Tyrosine
URIC ACID
VALINE
VERBASCOSE
VITAMIN B1
VITAMIN C
XANTHINE
XYLOPYRANOSE Of course, any number of other analytes could be tested for as well.

The sensor layer is preferably applied to the molded part as follows: A ruthenium dye complex such as that sold under the trade designation #206229 by Sigma is dissolved in ethanol as a solvent. A poly-methyl-methyl-acrylate (PMMA) such as that sold under the trade designation #182230 by Aldrich Chemical is dissolved in acetone as a solvent to create a 10-15% solution of polymer by weight. The ruthenium dye solution is then mixed into the PMMA polymer solution to create a solution that can be dip coated using an automated dip coater onto the tip of the optical member to create a stable oxygen sensitive coating.

An enzyme in a near neutral pH buffer such as glucose oxidase (among the sources of glucose oxidase is Fluka) is mixed with cellulose in bead form such as those cellulose beads sold under the trade designation #C-7204 by Sigma that have been crushed to approximately one micron in diameter to create a thick slurry of enzyme, cellulose and buffer. This slurry is then dip coated onto the optical member tip in the same manner as the oxygen sensitive coating.

The optical member is then further dip-coated into a gluteraldehyde solution such as that sold under the trade designation #01201-5 by Polysciences to chemically crosslink the enzyme and cellulose with the gluteraldehyde. The sensor is then allowed to dry in air or a desiccator overnight for the gluteraldehyde to polymerize sufficiently.

A final coating is then applied to the outside of the sensor tip using a poly-methyl-methyl-acrylate, chemically modified to include an acrylic acid group, that creates a stable and hard surface which protects the other coatings and allows diffusion of glucose and oxygen into the sensor. It is preferred that the modified poly-methyl-methyl-acrylate be that sold under the trade designation #37691-4 by Aldrich Chemical.

The signal produced by the interaction with the optical member and the analyte(s) is then passed to an optical detector such as a spectrometer such as that sold under the trade designation 52000 by Ocean Optics and then after interpretation of the signal by a suitable algorithm the data can then be displayed.

Note that the micro-invasive method is of particular advantage for immediate access to a sufficient quantity of fluid for measurement, unlike absorbing systems that require delays until sufficient quantity can be collected. Moreover, the optical tip under twenty microns is capable of entering into the stratum corneum without destruction of the large areas of the stratum corneum such as that of ablative means.

The method described above can be used to access both chemicals that our inherently found in biological systems and is also conceived to detect chemicals that a subject has been exposed to in the environment. The micro-invasive measurement is of particular advantage since chemicals which have invaded just to the level of the epidermis are still detectable where immediate detoxifying means can be employed to arrest further biological damage.

It should also be appreciated that microprobe 301 may be used for continuous analyte monitoring as well as for discrete monitoring. In the continuous mode of operation, the microprobe is secured to the body of the person being monitored such that the distal end of the probe is disposed and remains in the interstitial fluid of the person. The concentration of the desired analyte, such as glucose, is then continually monitored and may be displayed as desired (either continuously or upon demand).

In view of the above it will be seen that the various objects and features of the present invention are achieved and other advantageous results obtained. The description of the invention contained herein is illustrative only and should not be taken in a limiting sense.

What is claimed is:

1. An optical microprobe system for detecting at least one analyte in extra-cellular spaces comprising:
   a elongate microprobe body comprising a sensor head terminating in a distal optical tip adapted to enter the stratum corneum of the skin of a subject and extend toward the stratum basale of the skin terminating in extra-cellular spaces containing interstitial fluid, the elongate microprobe body comprising a micropipette tip, the micropipette tip comprising a conical base portion having a proximal and distal end, and a conical tip portion having a proximal and distal end with a substantial step configured where the conical base portion distal end meets the conical tip portion proximal end, the conical base portion distal end having a larger diameter than the conical tip portion proximal end, to cause the microprobe tip to stop in extra cellular spaces of the skin;
   a sensor layer covering the distal optical tip of the microprobe body, said sensor layer being adapted to interact with a predetermined analyte to be detected in the interstitial fluid;
   an optical detector within said distal optical tip sensor head and responsive to interaction of the sensor layer with the predetermined analyte to signal detection of said predetermined analyte.

2. The system as set forth in claim 1 wherein the microprobe body distal optical tip has a diameter no larger than approximately 10-50 microns.

3. The microprobe system as set forth in claim 1 further including a computer for analyzing the signal from the optical detector to determine the concentration of said analyte.

4. The microprobe system as set forth in claim 1 further including an electrically conductive member disposed in and extending to the exterior of the distal tip, said electrically conductive member being connected to a circuit for obtaining electrochemical measurements of an analyte in the interstitial fluid.

5. The microprobe system as set forth in claim 1 further including a plurality of optical distal tips for insertion into but not through the stratum basale of the subject, each optical distal tip its own sensor layer to provide multiple tests of analyte in the interstitial fluid.

6. The microprobe system as set forth in claim 1 wherein the sensor layer is sensitive to an analyte inherently found in biological systems.

7. The microprobe system as set forth in claim 1 wherein the sensor layer is sensitive to an environmental analyte not inherently found in biological systems.

8. The optical microprobe system of claim 1, wherein the microprobe body is formed of molded silica.

9. A method of detecting at least one analyte in extra-cellular spaces comprising:
   inserting an elongate microprobe sensor head comprising a micropipette tip, the micropipette tip comprising a conical base portion having a proximal end and a distal end and a conical tip portion having a proximal end and a distal end with a substantial step configured where the conical base portion distal end meets the conical tip portion proximal end, the conical base portion distal end having a larger diameter than the conical tip portion proximal end, to cause the microprobe to stop in extra cellular spaces of skin, a sensor layer covering the distal optical tip of the microprobe body, through the stratum corneum toward but not through the stratum basale of the skin of a subject into extra-cellular spaces containing interstitial fluid having at least one analyte to be detected,
   activating a light source and a detector, the light source and the detector disposed within the sensor head, and
   optically testing for a predetermined analyte in the extra-cellular space adjacent the distal end of the microprobe without drawing a sample of the interstitial fluid using the light source and the detector.

10. The method as set forth in claim 9 wherein said microprobe has a diameter no larger than approximately 10-50 microns.

11. The method as set forth in claim 9 wherein the microprobe is held in place with the distal end thereof in the interstitial fluid for a predetermined time, further including the step of monitoring the concentration of the analyte a plurality of times while the microprobe is held in place.

12. The method as set forth in claim 11 wherein the concentration of the analyte is continuously monitored during the time the microprobe is held in place with the distal end thereof in the interstitial fluid.

13. The method of claim 9, wherein the molding step further comprises molding the microprobe from silica.

14. The method of claim 9, wherein the molding step further comprises injection molding the microprobe.

15. The method of claim 9, wherein the molding step further comprises molding the elongate microprobe to correspond in shape to a mold having a conical base portion and a conical tip portion with a substantial step configured where the conical base portion meets the conical tip portion.

* * * * *